United States Patent [19]

Buck et al.

[11] 4,326,526

[45] Apr. 27, 1982

[54] DIALYSATE BAG ASSEMBLY FOR CONTINUOUS AMBULATORY PERITONEAL DIALYSIS

[75] Inventors: Robert T. Buck, Raleigh; Charles R. Horres, Chapel Hill, both of N.C.

[73] Assignee: Becton, Dickinson and Company, Paramus, N.J.

[21] Appl. No.: 188,394

[22] Filed: Sep. 18, 1980

[51] Int. Cl.³ ............................................. A61J 1/00
[52] U.S. Cl. ............................. 128/272; 128/213 A; 128/DIG. 24; 206/174
[58] Field of Search .............. 128/213 A, 213, 214 D, 128/272, 227, 272.3, DIG. 24; 206/170, 174, 175, 427, 428, 435; 229/27, 28 BC, 52 C

[56] References Cited

U.S. PATENT DOCUMENTS 3,087,491 4/1963 Gewelke et al. ........... 128/214 D X
3,187,750 6/1965 Tenczar, Jr. ....................... 128/272
3,255,923 6/1966 Soto ................................. 128/272 X
3,319,684 5/1967 Calhoun .......................... 128/272 X

*Primary Examiner*—Stephen C. Pellegrino
*Attorney, Agent, or Firm*—Richard J. Rodrick

[57] ABSTRACT

A dialysate bag assembly suitable for continuous ambulatory peritoneal dialysis includes a plurality of unfilled, expansible dialysate bags. An expansible container includes a plurality of compartments, each bag being removably positioned in one of those compartments. A filling feedline is detachably connected to each bag for providing dialysate from a source to each bag. The bags and the container are adapted to expand as the bags are being filled with the bags being engageable against the walls of the compartments to maintain the bags in relatively tight engagement. Each bag includes an opening for emptying dialysate which has been delivered to the same from the source.

15 Claims, 5 Drawing Figures

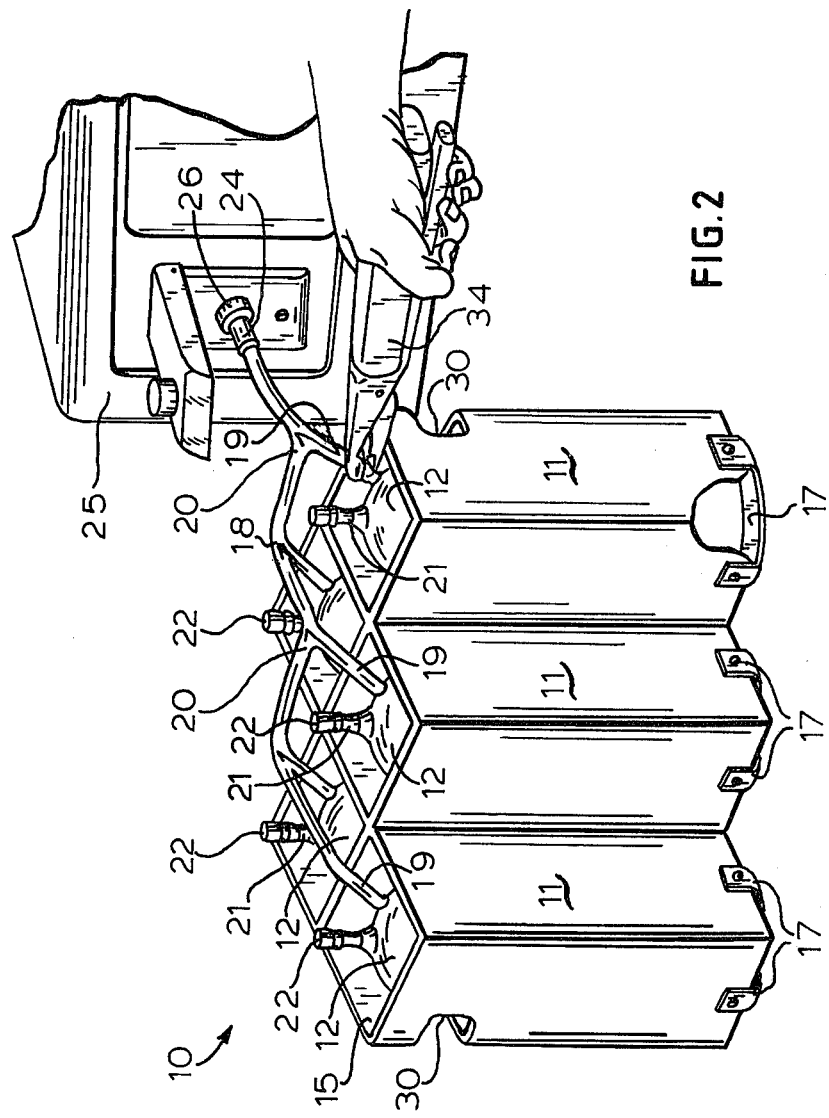

DIALYSATE BAG ASSEMBLY FOR CONTINUOUS AMBULATORY PERITONEAL DIALYSIS

BACKGROUND OF THE INVENTION

The present invention relates to a dialysate bag assembly and more particularly, concerns a plurality of dialysate bags in an assembly, arranged to be filled at the same time and suitable for the daily needs of a patient undergoing continuous ambulatory peritoneal dialysis.

With the advent of continuous ambulatory peritoneal dialysis (CAPD), more reliance is placed on the patient's independence and ability to handle the dialysis needs in the home, rather than in the hospital or doctor's office. The CAPD system used most frequently relies upon the delivery of dialysate from a flexible bag which the patient rolls up and wears during the time the dialysate is dwelling in the peritoneal cavity. During this dwell time, the patient has complete freedom of movement, even though the bag remains connected to the tubing inserted in the patient. When the dwell time has been completed, the patient allows the peritoneal cavity to drain with the used dialysate once again being collected into the flexible bag which the patient has unrolled. Once this dialysate collection is completed, the patient disconnects the used bag and contents, and connects a new, filled dialysate bag and starts the cycle over again. CAPD may require four (4) to five (5) dialysate exchanges daily of approximately two (2) liters at each exchange. Part of the independence which CAPD provides includes the reliance on the patient to prepare the dialysis according to the physician's prescription, fill the bags as needed from a delivery system and, of course, maintain the regimen which is required for satisfactory dialysis to treat the underlying condition of the patient. Providing a CAPD system for home use which is simple, non-complicated and convenient is the ultimate goal for this type of approach in dialysis. One of these conveniences is a system which would allow the patient to make his daily needs at one filling from the delivery system, rather than having to fill each bag separately that the patient will be using during the daily period. It is to such a daily dialysate bag approach that the present invention is directed.

U.S. Pat. No. 3,187,750 discloses a multiple bag blood storage unit which allows the filling of a plurality of plastic containers with blood from the main unit. No protective container assembly is disclosed in this patent which would also serve to assist the user in carrying the filled units. The blood bag system disclosed in the aforementioned patent requires a hermetic seal between the main storage unit and the conduit means which feeds the smaller containers. Such a hermetically sealed environment is not necessary in the home-type dialysis system, although an aseptic connection and filling technique is requisite for peritoneal dialysis.

SUMMARY OF THE INVENTION

A dialysate bag assembly suitable for continuous ambulatory peritoneal dialysis comprises a plurality of unfilled, expansible dialysate bags. An expansible container has a plurality of compartments, with each bag being removably positioned in one of the compartments. Filling means is detachably connected to each bag for providing dialysate from a source to each bag. The bags and the container are adapted to expand as the bags are being filled and are engageable against the walls of the compartments to maintain the bags in relatively tight engagement in the compartments. Each bag has means for emptying dialysate having been delivered to the same from the source.

In a preferred embodiment of the present invention, the expansible container is originally substantially flattened and includes a plurality of internal walls defining substantially equally sized compartments in a matrix configuration. Each bag in the compartments is also substantially flattened in the unfilled configuration. Preferably, each bag has a dialysate inlet opening and a dialysate outlet opening with a removable closure for each of the outlet openings. A main feedline is adapted to be connected at one end to a primary source for delivering dialysate to the bags. A secondary branch feedline preferably extends from the main feedline to the inlet opening on each of the bags. The bags, the main feedline and the secondary branch feedlines are preferably integrally formed of thermoplastic material with the walls of each secondary branch feedline being heat sealable to themselves to thereby provide a liquid-tight seal for each bag after the dialysate has been delivered.

In accordance with the principles of the present invention, a one-day supply of sterile dialysate can be delivered to individual bags at one mixing by the patient. For example, the CAPD patient can prepare the dialysis prescription in the in-home delivery system and then aseptically fill individual bags with this dialysate to cover the needs for the one day period. The container as part of this assembly serves a twofold function: during shipment and non-use before dialysate is performed, the present assembly is in a flattened condition to thereby conserve space. Inasmuch as each flattened bag is positioned inside a compartment, the container serves as an outer protective medium to prevent damage to the individual bags. After the bags have been filled with dialysate, the container serves as a storage unit for holding these filled bags and for allowing the patient to carry the filled bags as a single unit. Aseptic conditions are maintained after the bags are filled and during use by the patient. Of course, the bags may be removed from each of the compartments, for example, if the patient desires to leave the home and thereby place the bags in some type of pouch which is worn in belt-like fashion. Moreover, the main feedline, which is preferably integrally connected to each of the dialysate bags in order to maintain the aseptic conditions, especially during the filling procedure, is disposable after use so that the patient is not concerned with re-sterilizing a feedline which delivers dialysate from the delivery system. In addition, the system envisaged herein is non-complicated and requires a minimal number of steps for the patient to perform, along with a minimum number of tools to perform the sealing and separating functions for each individually filled dialysate bag.

BRIEF DESCRIPTION OF THE DRAWINGS

FIG. 2 is a perspective view of the dialysate bag assembly of FIG. 1 illustrated connected to a dialysate delivery system for filling purposes with the preferred technique for sealing the bags being shown;

DETAILED DESCRIPTION

Figure 1:
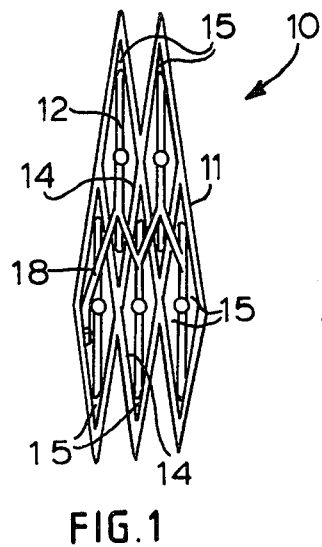
FIG. 1 is a top view illustrating the preferred dialysate bag assembly of the present invention in a substantially flattened condition as it would appear in shipment and storage.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, particularly FIG. 1, there is illustrated a dialysate bag assembly 10 which is suitable for use with patients on CAPD. Dialysate bag assembly 10 generally includes a container 11 and a plurality of dialysate bags 12.

Container 11 preferably has a plurality of internal walls 14 interconnected to each other in a matrix configuration. With container 11 being open at the top and bottom ends, the matrix configuration allows the container to collapse to a substantially flattened condition under the influence of squeezing pressure along the sides. On the other hand, this container may be expanded due to the flexible nature of internal walls 14 and the matrix configuration. As a result of this arrangement, a plurality of compartments 15 is formed within container 11 defined by internal walls 14. These compartments, when the container is in the flattened condition, essentially take on a flattened diamond shape, and when expanded, compartments 15 may be square or rectangular in shape. It is appreciated that the shape of the compartments is not critical and may take on different configurations depending upon the matrix-like, internal wall variations. It is preferred that container 11 be made of thin, flexible material such as lightweight plastic, cardboard, or the like.

In the preferred embodiment, the number of flexible dialysate bags 12 is equal to the number of compartments 15 in container 11, although this correspondence between bags and compartments is not necessary for the present invention. As seen in FIG. 1, dialysate bags 12 are also initially in a substantially flattened condition and are positioned so that each bag 12 is removably positioned in one of compartments 15. During shipment and storage before use, bags 12 and container 11 may be suitably wrapped (not shown) so that the bags will not fall out of the compartments or otherwise become damaged beforehand. Also, a flexible strap arrangement 17 may be provided at the bottom of the compartments to assure that the filled bags will not fall out during any transportation of the assembly. Other bottom supports may also be provided.

Figure 3:
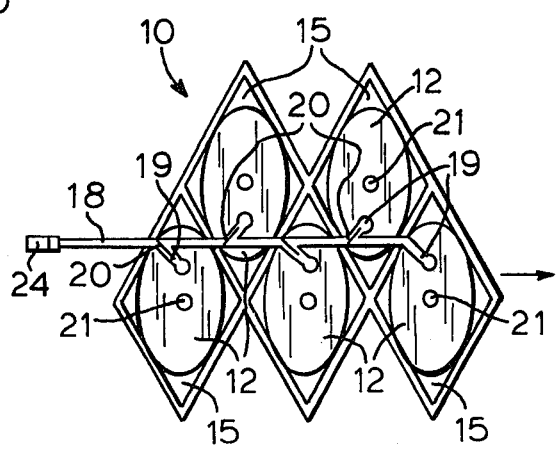
FIG. 3 is a top view similar to FIG. 1 illustrating the expansible nature of the dialysate bags and container during the filling operation.

As can be seen more clearly in FIGS. 2 and 3, taken in conjunction with FIG. 1, flexible dialysate bags 12 are interlinked to each other by virtue of a main feedline 18. This feedline is preferably a length of hollow flexible tubing which has a plurality of secondary branch feedlines 19 integrally connected to and formed as part of the main feedline. The number of secondary branch feedlines 19 corresponds to the number of dialysate bags 12 since each secondary branch feedline is also preferably integrally connected to one of the dialysate bags. At each connection of secondary branch feedline 19 to dialysate bag 12, an inlet opening is formed so that dialysate can be delivered to the interior of each bag during the filling operation. The main feedline, secondary branch feedlines and dialysate bag arrangement is preferably a unitary structure in which the entire arrangement is formed in a single molding process. Most desirably, a flap valve 20 is formed inside main feedline 18 and extends a short distance into the various secondary branch feedlines 19 thereby serving as a directional valve. The purpose of this valving arrangement will be discussed more fully hereinafter.

In the embodiment being described, each dialysate bag 12 also includes a dialysate outlet opening 21 in order to be able to empty dialysate from each bag which has been filled. A suitable closure 22 is provided in each outlet opening 21, which is removable during the emptying process and which serves to provide a liquid-tight seal when the dialysate is contained within the bag. A separate outlet opening is required in the dialysate bags being described only when the dialysate inlet opening is permanently sealed closed; otherwise, there are embodiments within the purview of this invention in which one opening may serve as both inlet and outlet openings for the dialysate to respectively enter and empty from the bags.

Main feedline 18 as described herein includes a connector 24 at its free end. Referring now specifically to FIG. 2, dialysate bag assembly is illustrated being filled with dialysate delivered from a typical home-type delivery system 25. Main feedline connector 24 is connected to a mating connector 26 mounted on delivery system 25. A primary source of dialysate is prepared by the patient or otherwise, and is provided to delivery system 25. By appropriate controls on the delivery system (not shown, but well known) dialysate is delivered to each of bags 12 which are in fluid communication with main feedline 18. As each bag is filled with dialysate, the internal volume increases and causes an expansion of the bag due to its flexible nature. This expansion of the bags concurrently expands container 11 which is allowed to expand due to its matrix configuration. As can be seen more clearly by referring to FIG. 3, the size characteristics of dialysate bags 12 and compartments 15 are significant during the expanding phase of the filling operation. As bags 12 expand they come in contact with the walls of the compartments. This produces a relatively snug engagement whereby each bag is maintained in a relatively tight position in the compartment, even after the feedlines have become disconnected. However, this engagement while providing a snug fit, still allows the patient to remove the dialysate bag from the compartment when it is ready to be used. Straps 17 at the bottom of the compartments assist in preventing the filled bags from falling out.

In the preferred embodiment of the present invention as illustrated in the drawings, valve 20, serving as a diverter, allows the dialysate from the delivery system to fill substantially one bag at a time. For instance, since valve 20 extends into the secondary branch feedline, dialysate will travel through the main feedline and then into the secondary branch feedline until the first bag next to the delivery system is filled. When this filling is complete, flow of dialysate will then travel on the other side of valve 20 and back up secondary branch feedline 19 and once again into main feedline 18 between the first and second dialysate bags. Next, the second bag adjacent the delivery system is filled in the same fashion. This procedure continues until each of the dialysate bags is filled in succession as long as a valve arrangement, as illustrated, is included in the various feedlines. Of course, without such a valve arrangement, all of the dialysate bags would be filled in a parallel filling arrangement rather than in succession.

In order to make the carrying and transporting of assembly 10 more convenient, handles are formed in container 11 by notches 30 at opposite ends thereof. These notches become more pronounced when container 11 expands thereby providing an easier grip for the user.

Figure 4:
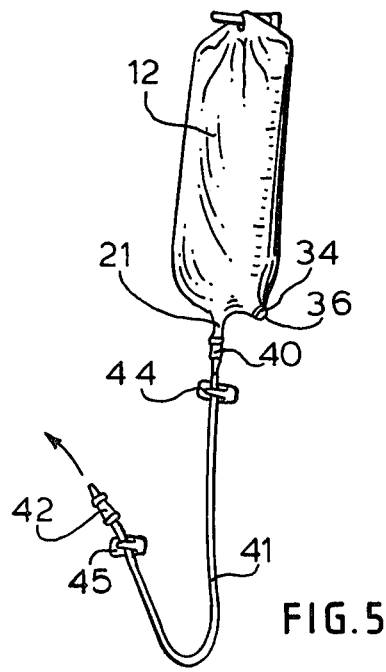
FIG. 4 is a perspective view illustrating one technique of separating each filled bag after it has been sealed.

In the embodiment being described, the preferable material for the integral unit of dialysate bags, main feedline and secondary branch feedlines is a thermoplastic material such as polyvinyl chloride. However, other materials may be chosen, such as embossed polyurethane in order to minimize leaching of plasticizer into the dialysate. This material is most desirable since it can be suitably heat fused. In particular, after the bags have been filled with dialysate, it is necessary to seal the inlet opening to each bag so that the bag becomes liquid-tight. To this end, a suitable heating element 32, as illustrated in FIG. 2, is employed to grip each secondary branch feedline in order to compress the walls of the secondary feedline together, thereby displacing the dialysate contained therein. Sufficient heat supplied through heating element 32 thereby melts the thermoplastic material and fuses the walls of the tubing together in a liquid-tight seal. After heat is removed from heat gun 32, the walls will cool and remain in the fused, sealed configuration. This configuration is essentially a flattened segment 34 in secondary feedline 19 as more clearly seen in FIG. 4. After this sealing step has been performed, each bag is separated from the feedlines and thereby from each other by a suitable cutting operation along the sealed flat segment 34. A scissors 35, or similar tool, may be employed such as illustrated in FIG. 4. The cut is preferably made through flat segment 34 thereby leaving a short stub 35 at the inlet opening as more clearly illustrated by referring to FIG. 5. Other means, such as mechanical clamps, to seal the inlet opening of the dialysate bags and to partition same from the feedlines are readily conceivable and fall within the purview of this invention.

A convenient technique is available to assure, after filling, that the system filled each bag aseptically. For instance, a heat seal can be placed above and below of tubing 19 near the bag thereby retaining a sample between sealed segments for later evaluation.

Figure 5:
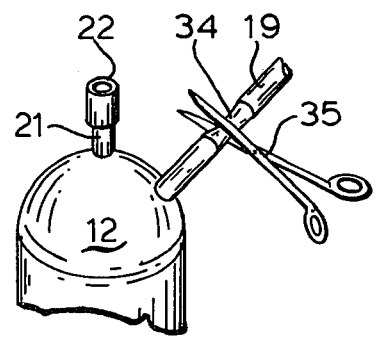
FIG. 5 is a perspective view illustrating an individual, filled bag as it may appear when ready for use on a CAPD patient.

In FIG. 5 a filled, separated dialysate bag is illustrated as it may appear during use by a CAPD patient. Filled bag 12 is customarily hung or mounted so that outlet opening 21 faces downwardly for reliance on gravity feed of the dialysate in the bag. The CAPD patient removes closure 22 from outlet opening 21 before mounting the bag, and connects delivery tubing 41 which will serve as the conduit between dialysate bag 12 and the patient's peritoneal cavity. Tubing 41 includes a pair of appropriate connectors, a connector 40 on one end which mates with outlet opening 21 on the bag, and a second connector 42 on the opposite end of the tubing which is provided for direct connection to the delivery mechanism inserted into the patient. Appropriate clips 44 and 45 may be provided for control of the dialysate from the bag being delivered to the patient, and also when the used dialysate is thereafter collected, once again, into the bag.

It also may be practicable to provide an outlet tubing section as an integral part of the bag which would couple to the patient's catheter. This would then eliminate one connection step.

Although the drawings illustrate five compartments in container 11 and five dialysate bags 12, this number may vary according to the prescription needs of each patient on CAPD. For example, a typical CAPD patient requires four to five dialysate exchanges daily of two (2) liters at each exchange. Therefore, for the patient's daily needs, the present invention would have at least four compartments in the container along with four dialysate bags, each bag preferably holding at least two (2) liters of the prescribed dialysate.

Thus, the present invention provides a dialysate bag assembly which conveniently serves a CAPD patient's needs for one day as far as filling and storing the filled dialysate bags. Before filling, the present invention requires minimal storage space and packaging. Furthermore, the dialysate feedline connection of the present invention is separable from the dialysate bags after filling, is disconnectable from the dialysate delivery system and is, moreover, disposable after the dialysate bags have been filled. As a result, aseptic filling of the dialysate bags is readily facilitated.

What is claimed is:

1. A dialysate bag assembly for continuous ambulatory peritoneal dialysis comprising:
a substantially flattened, expansible container having a plurality of compartments;
a plurality of substantially flattened, expansible dialysate bags, each bag being removably positioned in one of said compartments, each bag having a dialysate inlet opening and a dialysate outlet opening with removable closure means to close said outlet openings;
a main feedline adapted to be connected at one end to a primary source for delivering dialysate to said bags, said feedline being detachably connected to said inlet opening on each of said bags for filling same with dialysate, said bags and said container adapted to expand as said bags are being filled; and
means associated with each of said inlet openings to close same in liquid-tight fashion after the delivery of dialysate is completed.

2. The assembly of claim 1 wherein said container is open at the bottom and top and includes a plurality of internal walls defining substantially equally sized compartments in a matrix configuration.

3. The assembly of claim 2 wherein the bottom of the container includes support means for supporting the bags and preventing same from falling out of the compartments.

4. The assembly of claim 2 wherein said bags and said compartments are sized so that upon expansion said bags frictionally engage the walls in the compartment to maintain each bag in relatively tight engagement in the respective compartments.

5. The assembly of claim 1 wherein said container includes handle means for carrying said assembly.

6. The assembly of claim 5 wherein said handle means are notches at opposite ends of the container which provide a grip for a user after the container has expanded.

7. The assembly of claim 1 wherein said feedline is integrally connected to each of said inlet openings.

8. The assembly of claim 1 wherein each of said integral connections is a secondary branch feedline extending from said main feedline to the inlet opening on each bag.

9. The assembly of claim 1 wherein said main feedline, secondary branch feedlines and dialysate bags are integrally formed and are made of thermoplastic material.

10. The assembly of claim 9 wherein the walls of each secondary branch feedline are heat sealable to themselves to thereby provide the means to seal each inlet opening after dialysate is delivered to the bags, said secondary branch feedlines adapted to be separated from said main feedline after said walls are sealed.

11. The assembly of claim 1 wherein there are at least four compartments in said container.

12. A dialysate bag assembly suitable for continuous ambulatory peritoneal dialysis comprising:
   a plurality of unfilled, expansible dialysate bags;
   an expansible container having a plurality of compartments, each bag being removably positioned in one of said compartments; and
   filling means detachably connected to each bag for providing dialysate from a source to each bag, said bags and said container adapted to expand as said bags are being filled, with said bags being engageable against the walls of the compartments to maintain the bags in relatively tight engagement in said compartments, each bag having means for emptying dialysate having been delivered to same from said source.

13. A dialysate bag assembly for continuous ambulatory peritoneal dialysis comprising:
   a substantially flattened, expansible container having a plurality of internal walls defining substantially equally sized compartments in a matrix configuration;
   a plurality of substantially flattened unfilled, expansible dialysate bags, each bag being removably positioned in one of said compartments, each bag having a dialysate inlet opening and a dialysate outlet opening with a removable closure for each of said outlet openings;
   a main feedline adapted to be connected at one end to a primary source for delivering dialysate to said bags; and
   a secondary branch feedline extending from said main feedline to the inlet opening on each of said bags, said bags, main feedline and secondary branch feedlines being integrally formed of thermoplastic material with the walls of each secondary branch feedline being heat sealable to themselves to thereby provide a liquid-tight seal for each bag after the dialysate has been delivered, said secondary branch feedlines adapted to be separated from said main feedline after said walls are sealed whereby each filled bag is adapted to be separated from each other.

14. The assembly of claims 8 or 13 wherein each secondary branch feedline includes a directional valve positioned therein near the juncture with said main feedline so that dialysate flows into the bag closest to said primary source first and completely fills same before the dialysate is delivered to an adjacent bag.

15. The assembly of claims 1 or 13 wherein each bag is adapted to hold about two (2) liters of dialysate when filled.

* * * * *